United States Patent [19]

Iwinski

[11] Patent Number: 5,425,289
[45] Date of Patent: Jun. 20, 1995

[54] BUNG TOOL

[75] Inventor: Dean J. Iwinski, Muskego, Wis.

[73] Assignee: Snap-on Incorporated, Kenosha, Wis.

[21] Appl. No.: 139,093

[22] Filed: Oct. 21, 1993

[51] Int. Cl.⁶ .................................................. B67B 7/14
[52] U.S. Cl. ........................................ 81/3.4; 81/461;
81/439; 81/176.15; 81/124.5
[58] Field of Search ................... 81/3.07, 3.4, 176.1,
81/176.15, 125.1, 438, 439, 461, 124.5, 121.1,
124.2

[56] References Cited

U.S. PATENT DOCUMENTS

| | | | |
|---|---|---|---|
| 2,383,573 | 8/1945 | Tomsek | 81/176.15 |
| 2,421,665 | 6/1947 | Umbdenstock | 81/176.15 |
| 2,445,978 | 7/1948 | Stellin . | |
| 2,643,566 | 6/1953 | Dos Santos et al. . | |
| 3,564,949 | 2/1971 | Hedrick | 81/461 X |
| 3,733,938 | 5/1973 | Smith | 81/124.5 X |
| 4,625,599 | 12/1986 | Icard . | |
| 4,759,122 | 7/1988 | Weintraub . | |
| 5,099,726 | 3/1992 | Hsiao . | |
| 5,134,905 | 8/1992 | Brennan et al. . | |
| 5,168,782 | 12/1992 | Cromwell . | |
| 5,172,615 | 12/1992 | Albrecht . | |

FOREIGN PATENT DOCUMENTS

| | | | |
|---|---|---|---|
| 0477380 | 10/1951 | Canada | 81/176.15 |
| 0725392 | 1/1966 | Canada | 81/176.15 |
| 2193134 | 2/1988 | United Kingdom | 81/176.1 |

OTHER PUBLICATIONS

Snap-on Tools catalog p. 93 (1993).

Primary Examiner—James G. Smith
Attorney, Agent, or Firm—Emrich & Dithmar

[57] ABSTRACT

A bung tool has a cylindrical body with a four-armed drive portion projecting from one end thereof and a six-armed drive portion projecting from the opposite end thereof, respectively for engagement with different types of bungs. A drive member reciprocates in a square cross-section axial bore through the body, being manually moveable by a handle which projects radially through a slot in the body. The drive lug of an associated drive lever is receivable in the opposite ends of the bore for respectively driving the two drive portions. The drive member reciprocates among two recessed positions respectively spaced from the opposite ends of the bore to allow insertion of the drive lug therein and a drive position projecting from one of the drive portions for driving engagement with a bung cap.

13 Claims, 2 Drawing Sheets

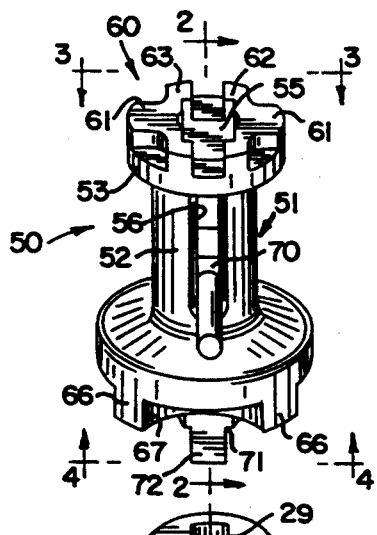
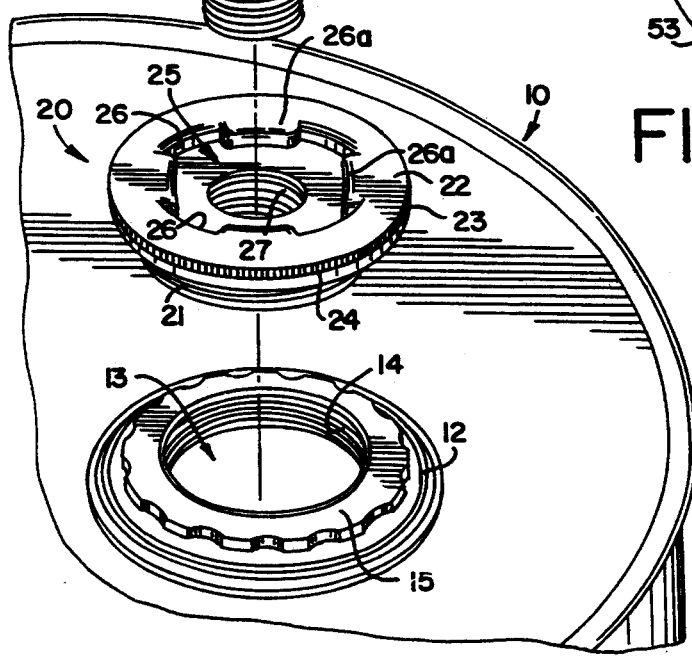

BUNG TOOL

BACKGROUND OF THE INVENTION

1. Field of the Invention

The present invention relates to tools for inserting and removing screw-in drum plugs or bungs. In particular, the invention relates to a bung socket of the type which is adapted to be used with an associated drive lever, such as a ratchet wrench, a breaker bar or the like.

2. Description of the Prior Art

Bungs are closures for access openings in tanks, drums, pipes and the like. Heretofore such bungs have commonly been provided with a circular cavity or recess with a diametrically extending rib thereacross or projections extending radially thereinto from diametrically opposed locations. Tools have been provided for operating such bungs, the tool including a pair of arms which straddle the rib or projections on the bung and engage them for rotation. One such tool is sold by Snap-on Tools Corporation under Model A172A. That tool is designed to work with a number of different variants of the above-described bung configuration. Many bungs are provided with an internally threaded central well which is closed by a separate cap. The aforementioned Snap-on Tool has a spring-loaded central projection adapted for engagement with a recess in the cap, this projection being retractable against the urging of a bias spring when the tool is being used for rotating the bung itself.

More recently, a number of different styles of bung have come into use. These bungs have a drive recess in the end wall thereof, the recess having a number of laterally outwardly extending lobes of various configurations. Fundamentally, most of the bungs are either of a four-lobed or a six-lobed configuration. Prior bung tools are not usable with these new bung configurations.

SUMMARY OF THE INVENTION

It is a general object of the invention to provide an improved bung tool which avoids the disadvantages of prior tools while affording additional structural and operating advantages.

An important feature of the invention is the provision of a bung tool which is usable with a number of different types of modern bung configurations.

In connection with the foregoing feature, another feature of the invention is the provision of a bung tool which has a plurality of differently-configured drive portions projecting therefrom.

In connection with the foregoing feature, another feature of the invention is the provision of a bung tool of the type set forth, which is usable with an associated drive lever for driving any of the several drive portions.

Yet another feature of the invention is the provision of a bung tool of the type set forth, wherein at least one of the drive portions is retractable.

These and other features of the invention are attained by providing a bung tool comprising: a body, a first bung-engaging drive portion projecting from the body in a first direction and having a first plurality of arms extending transversely of the first direction, and a second bung-engaging drive portion configured differently from the first drive portion and projecting from the body in a second direction and having a second plurality of arms extending transversely of the second direction.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 1 is a perspective view of the bung tool of the present invention with its cap drive member extended and shown associated with a fragmentary portion a drum with a bung and cap of a type with which the tool is usable illustrated in exploded form;

FIG. 2 is an enlarged view in vertical section of the tool of FIG. 1, taken along the line 2—2 therein and with the fully retracted position of the cap drive bar shown in phantom;

FIG. 3 is a top plan view of the tool of FIG. 2;

FIG. 4 is a bottom plan view of the tool of FIG. 2;

DESCRIPTION OF THE PREFERRED EMBODIMENT

Figure 6:
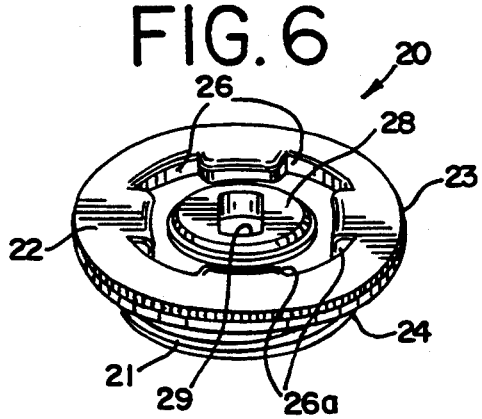
FIG. 6 is a perspective view of the bung of FIG. 1 with its cap installed.

Referring to FIG. 1, there is illustrated a drum 10, having a lid 11 provided with a bung hole fitting 12 defining an access hole 13 into the drum 10 which is provided with an internal thread 14, the fitting 12 having an outer annular end wall 15. Referring also to FIG. 6, a drum plug or bung 20 is designed to close the hole 13. The bung 20 has a cylindrical side wall 21 which is externally threaded for threaded engagement with the fitting 12. The bung 20 has a circular end wall 22 which defines an annular flange 23 against which is seated a gasket 24 for sealing engagement with the end wall 15 of the bung hole fitting 12. The end wall 22 is provided with a central drive recess 25 which is generally cruciform in shape, defining four equiangularly spaced-apart lobes 26 separated by radially inwardly extending projections 26a. Formed centrally of the bung 20 is an internally threaded cylindrical well 27 which extends axially inwardly from the bottom of the recess 25 coaxially with the cylindrical wall 21. The well 27 defines an auxiliary port through the bung 20 which may be used for testing purposes, drawing off samples of contents of the drum and the like. The well 27 is closed by a threaded cap 28 provided with a generally rectangular drive recess 29 in its outer end.

Figure 7:
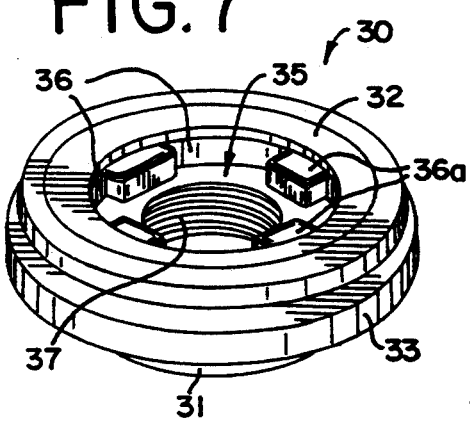
FIG. 7 is a perspective view of another type of four-lobed bung of the type of which the tool of FIG. 1 is usable.

Referring to FIG. 7, there is illustrated another version of four-lobed bung, generally designated by the numeral 30, of the type with which the present invention is intended to be used. The bung 30 has an externally threaded cylindrical wall 31 and a circular end wall 32 provided at its outer perimeter with a depending cylindrical skirt 33 designed for engagement with a different type of bung hole fitting. Formed centrally in the end wall 32 is a drive recess 35 which is generally cruciform in shape, having four equiangularly spaced-apart lobes 36 which are defined by four radially inwardly extending projections 36a. An internally threaded cylindrical well 37 is formed in the bottom of the recess 35 coaxially with the cylindrical wall 31. It will be appreciated that the well 37 may be closed by a suitable cap (not shown) which may be of the same type as that illustrated in FIGS. 1 and 6.

Figure 8:
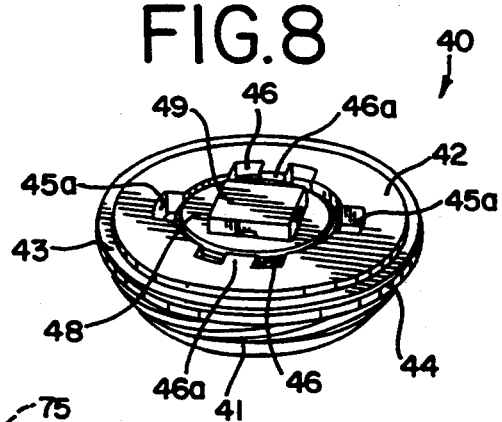
FIG. 8 is a perspective view of a six-lobed bung of the type with which the tool of FIG. 1 is usable.

Referring to FIG. 8, there is illustrated another type of bung, generally designated by the numeral 40, with which the present invention may be used. The bung 40 has an externally threaded cylindrical wall 41 closed by a circular end wall 42 which defines a flange 43 against which is seated a gasket 44 for sealing engagement with the end wall 15 of the bung hole fitting 12 or one similar thereto. The end wall 42 is provided with a drive recess 45 which has six lobes. More specifically, the recess 45 has two diametrically spaced-apart, relatively wide lobes 45a, and four relatively narrow lobes 46 arranged in two pairs, with the lobes of each pair separated by radially inwardly extending projections 46a, which projections are diametrically opposed along a diameter perpendicular to that along which the lobes 45a are aligned. The lobes of one pair of lobes 46 are respectively aligned with those of the other pair along chords of the circular end wall 42, respectively disposed on either side of the diameter along which the projections 46a are aligned. Formed centrally in the recess 45 is an internally threaded cylindrical well (not shown) of the same type as was describe above in connection with FIGS. 6 and 7, and which is closed by an externally threaded cap 48 provided with an axially outwardly projecting square drive lug 49. It will be appreciated that the cap 48 could also be provided with a drive recess like that disclosed in the cap 28.

It will be appreciated that there are other four-lobed and six-lobed bung configurations with which the present invention may be used, but the foregoing will serve to illustrate the general configuration of such bungs.

Referring now also to FIGS. 2–5, there is illustrated a bung tool 50, constructed in accordance with and embodying the features of the present invention. The tool 50 has a body 51 including a cylindrical tube 52 integral at one end thereof with an annular flange 53 and at the other end thereof with a larger annular flange 54. Formed axially through the body 51 is a bore 55 which is substantially square in transverse cross section. Formed in the side wall of the tube 52 is an axially extending elongated slot 56 which communicates with the bore 55. Formed in the walls of the bore 55 are three sets of arcuate detent recesses 57, 58 and 59, the sets being respectively disposed adjacent to the flange 53, adjacent to the end of the slot 56 which is nearest the flange 54, and adjacent to the axial outer edge of the flange 54. Each set of recesses 57-59 includes four recesses respectively disposed in the four faces of the bore 55.

The body 51 includes a drive portion 60 projecting axially outwardly from the flange 53 and comprising six laterally extending arms. More specifically, the drive portion 60 has a pair of relatively wide arms 61 disposed at diametrically opposed locations along the flange 53, and two pairs of relatively thin arms 62 and 63, respectively disposed perpendicular to and intersecting the arms 61. The arms 62 are aligned along a chord of the flange 53, while the arms 63 are aligned along another chord of the flange 53, the chords lying on opposite sides of a diameter which is disposed perpendicular to the diameter along which the arms 61 are aligned. The adjacent end of the bore 55 extends through the drive portion 60 and is provided with a shallow frustoconical counterbore which defines chamfered portions 64 to facilitate entry of a drive lever into the bore 55 in a manner which be explained more fully below.

The body 51 is also provided at the opposite end thereof with a drive portion 65 which projects axially outwardly from the flange 54. The drive portion 65 is generally cruciform in shape, defining four radially outwardly extending and equiangularly spaced-apart arms 66, the junctions between the arms 66 being defined by arcuate outer walls 67. The bore 55 also extends through the drive portion 65 and is provided thereat with a shallow frustoconical counterbore which defines chamfered portions 69.

Figure 9:
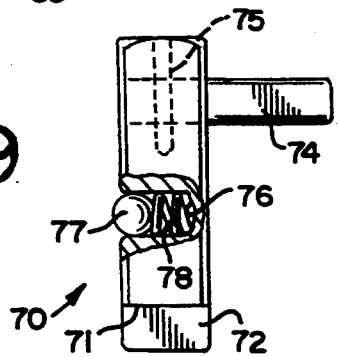
FIG. 9 is a side elevational view in partial section of the cap drive bar of the tool of FIG. 1.

Referring also to FIG. 9, slidably disposed in the bore 55 is an elongated slide bar 70, substantially square in transverse cross section and preferably having truncated corners. The slide bar 70 has a length which is substantially less than that of the bore 55, and the end thereof toward the flange 54 is provided with a pair of rectangular notches or recesses 71 on the opposite sides thereof, which define a reduced-thickness drive end 72 (FIGS. 2, 4, 5 and 9). Extending through the slide bar 70 adjacent to the other end thereof is a cylindrical bore 73 in which is disposed an actuator pin 74, which is retained in place by a spring pin 75 seated in an axial bore in the adjacent end of the slide bar 70. The actuator pin 74 projects laterally outwardly through the slot 56 a predetermined distance sufficient to be manually grasped by a user. Formed laterally in the side of the slide bar 70 opposite the slot 56 and intermediate the ends of the slide bar 70 is a cylindrical recess 76 in which is seated a detent ball 77 and a helical compression spring 78. The spring 78 resiliently urges the ball 77 laterally outwardly and the ball 77 is retained by an annular lip at the end of the recess 76, all in a known manner.

It will be appreciated that, by use of the actuator pin 74, the slide bar 70 may be axially reciprocated in the bore 55 among three operating positions: (1) a fully-recessed position illustrated in broken line in FIG. 2, wherein the actuator pin 74 is at the end of the slot 56 adjacent to the flange 53; (2) a recessed position illustrated in FIG. 5, wherein the actuator pin 74 is disposed intermediate the ends of the slot 56 and the detent ball 77 is seated in one of the detent recesses 58; and (3) a drive position, illustrated in solid line in FIG. 2, wherein the actuator pin 74 is disposed at the end of the slot 56 adjacent to the flange 54, the detent ball 77 being seated in one of the detent recesses 59, and the drive end 72 of the slide bar 70 projecting axially outwardly beyond the drive portion 65 a predetermined distance.

In operation, the tool 50 is adapted to be rotatably driven about its longitudinal axis by an associated drive lever, which may be in the form of a ratchet wrench 80, (FIG. 5), a breaker bar (not shown), or the like. More specifically, referring to FIG. 5, the ratchet wrench 80 or other associated lever has a square drive lug 85 which is receivable in either end of the bore 55, the drive lug 85 typically having a detent ball (not shown) which is receivable in the associated one of the detent recesses 57 or 59, in a known manner, to resiliently retain the drive lug 85 in engagement with the tool 50.

Figure 5:
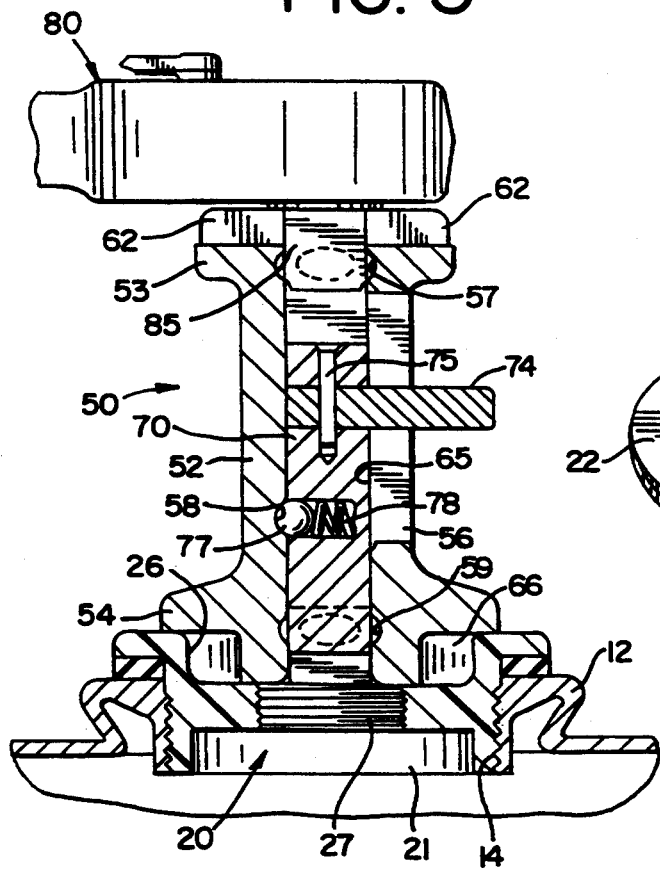
FIG. 5 is view similar to FIG. 2 with the cap drive bar shown in its intermediate position and with the tool shown in engagement with an associated bung and engaged with a drive lever.

As can be seen from the drawings, when the slide bar 70 is disposed in its partially-retracted or intermediate position, illustrated in FIG. 5, the slide bar 70 is spaced a sufficient distance from the end of the bore 55 nearest the actuator pin 74 to accommodate insertion of the drive lug 85. However, the opposite end of the slide bar 70 is spaced closely adjacent to the opposite end of the bore 55 so as to prevent insertion of the drive lug 85. Thus, in order to insert the drive lug 85 into this opposite end of the bore 55, the slide bar 70 is moved to its fully retracted position, illustrated in broken line in FIG. 2. Accordingly, in order to operate a four-lobed bung of the type illustrated in FIGS. 1 and 5–7, the slide bar 70 is disposed in its position illustrated in FIG. 5 and the drive lug 85 is mounted in place as shown. Then the drive portion 65 is fitted in the recess 25 of the bung 20 or the recess 35 of the bung 30, with the arms 66 respectively disposed in the lobes 26 (or 36) for engagement with the projections 26a (or 36a). Thus, it will be appreciated that rotation of the tool 50 by the ratchet wrench 80 will effect the corresponding rotation of the bung 20 (or 30) in a known manner.

Similarly, if it is desired to operate a six-lobed bung such as the bung 40 illustrated in FIG. 8, the slide bar 70 is moved to its fully retracted position, illustrated in broken line in FIG. 2, and the lever drive lug 85 is inserted through the drive portion 65 into the adjacent end of the bore 55. Then, the drive portion 60 is inserted in the recess 45 of the bung 40, with the arms 61 respectively seated in the lobes 45a and the arms 62 and 63 respectively seated in the lobes 46 for rotation of the bung 40 in a known manner.

Finally, when it is desired to operate a cap, such as the cap 28, the slide bar 70 is moved to its drive position illustrated in solid line in FIG. 2, and the drive end 72 thereof is inserted in the cap drive recess 29. The drive lug 85 of the drive lever will be inserted through the drive portion 60 into the adjacent end of the bore 55, as shown in FIG. 5. It will be appreciated that the chamfered portions 64 and 69 facilitate insertion of the drive lug 85 into the ends of the bore 55.

In the event that the bung has a cap, such as a cap 48, with a drive lug 49, it will be appreciated that the drive lug 49 can be seated in the appropriate end of the bore 55 if it is of an appropriate size, and the tool 50 can then be used to operate that cap. Otherwise, a separate socket fitting will be necessary to engage the drive lug 49.

From the foregoing, it can be seen that there has been provided an improved bung tool which is of simple and economical construction and is adapted for operation with a number of different configurations of modern bungs and associated caps.

I claim:

1. A bung tool comprising: a body, a first bung-engaging drive portion projecting from said body in a first direction and having a first plurality of arms extending transversely of said first direction, a second bung-engaging drive portion configured differently from said first drive portion and projecting from said body in a second direction and having a second plurality of arms extending transversely of said second direction, a third bung-engaging drive portion configured differently from said first and second drive portions and mounted on said body for movement between a retracted position recessed within said body and a drive position projecting from said body, and handle means coupled to said third drive portion for facilitating manual movement thereof between the retracted and drive positions thereof.

2. The tool of claim 1, wherein said third drive portion projects from said body in said first direction.

3. The tool of claim 2, wherein said third drive portion projects through said first drive portion.

4. The tool of claim 1, wherein said body includes means mounting said third drive portion for reciprocating movement between the retracted and drive positions thereof.

5. The tool of claim 4, wherein said third drive portion reciprocates parallel to said first direction.

6. The tool of claim 5, wherein said first and second directions are substantially coaxial.

7. A bung tool comprising: a body, a first bung-engaging drive portion projecting from said body in a first direction and having a first plurality of arms extending transversely of said first direction, a second bung-engaging drive portion configured differently from said first drive portion and projecting from said body in a second direction and having a second plurality of arms extending transversely of said second direction, said body having a bore extending therethrough and shaped and dimensioned for receiving in the opposite ends thereof a drive lug of an associated drive lever, and a drive member disposed in said bore for movement therein among first and second and third positions, said drive member in its first position being recessed within said body and spaced from one end of said bore a distance sufficient to accommodate reception of a drive lug therein, said drive member in its second position being recessed within said body and spaced from the other end of said bore a distance sufficient to accommodate reception of a drive lug therein, said drive member in its third position projecting from said body at said one end of said bore and spaced from the other end of said bore a distance sufficient to accommodate reception of a drive lug therein.

8. The tool of claim 7, wherein said bore is substantially square in transverse cross section.

9. The tool of claim 7, wherein said body has a slot formed therein communicating with said bore, and further comprising a handle member coupled to said drive member and projecting through said slot to facilitate manual movement of said drive member among the positions thereof.

10. The tool of claim 7, wherein said first and second directions are substantially coaxial.

11. The tool of claim 10, wherein said drive member in its third position projects through said first drive portion.

12. The tool of claim 7, and further comprising detent means yieldably retaining said drive member in each of its second and third positions.

13. The tool of claim 7, wherein said first plurality of arms is different in number from said second plurality of arms.

* * * * *